United States Patent
Deline et al.

(10) Patent No.: US 6,384,279 B1
(45) Date of Patent: May 7, 2002

(54) SYNTHESIS OF A TETRAAMIDO MACROCYCLE LIGAND FROM A NOVEL DIAMIDODIOL

(75) Inventors: James E. Deline, Livermore; Michael M. Ott, Oakland, both of CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 09/943,536

(22) Filed: Aug. 30, 2001

Related U.S. Application Data

(62) Division of application No. 09/347,435, filed on Jul. 2, 1999, now Pat. No. 6,297,400.

(51) Int. Cl.$^7$ .................... C07C 231/02; C07C 51/16
(52) U.S. Cl. .................... 564/142; 564/143; 564/155; 564/159; 564/160; 562/408; 562/409; 562/418; 562/538; 562/565
(58) Field of Search ................ 564/160, 155, 564/159, 142, 143; 562/408, 409, 418, 538, 565

(56) References Cited

U.S. PATENT DOCUMENTS 5,853,428 A  12/1998 Collins et al. .................. 8/107

FOREIGN PATENT DOCUMENTS

JP    9-255668    *  9/1997

OTHER PUBLICATIONS

Denmark et al, J. Org. Chem, vol. 60, 4884–4892, 1995.*

Collins et al., "Stable Highly Oxidizing Cobalt Complexes of Macrocyclic Ligands," J. Am. Chem. Soc., 1991, vol. 113, pp. 8419–8425.

* cited by examiner

*Primary Examiner*—Shailendra Kumar
(74) *Attorney, Agent, or Firm*—Joel J. Hayashida; Mark E. Baze

(57) ABSTRACT

A new composition of matter for a diamidodiol and a method for preparing the diamidodiol. The exemplary diamidodiol has the formula $C_{15}H_{30}N_2O_4$ and is prepared by reacting a first quantity of 2-amino-2-methyl-1-propanol with a second quantity of a di-substituted malonyl dichloride (i.e., diethylmalonyl dichloride), preferably in ethyl acetate as solvent. A tetraamido macrocycle is prepared from the diamidodiol in two steps by oxidizing the diamidodiol to form a diacid followed by coupling using a known procedure of the diacid with an aryl diamine (e.g., 1,2-diaminobenzene) to yield the tetraamido macrocycle.

11 Claims, 2 Drawing Sheets

SYNTHESIS OF A TETRAAMIDO MACROCYCLE LIGAND FROM A NOVEL DIAMIDODIOL

This is a division, of application Ser. No. 09/347,435, filed Jul. 2, 1999, now U.S. Pat. No. 6,297,400 entitled "Improved Synthesis of a Tetraamindo Macrocycle Ligand From A Novel Diamidodiol".

FIELD OF THE INVENTION

The present invention relates to tetraamido macrocyclic ligands that form complexes with transition metals, and more particularly to the synthesis of a novel diamidiol that is used as a substrate in an improved synthesis of macrocycles such as exemplified by 5,6-Benzo-3,8,11,13-tetraoxo-2,2,9,9-tetramethyl-12,12-diethyl-1,4,7,10-tetraazacyclotridecane, $H_4$.

BACKGROUND OF THE INVENTION

The use of transition metal chelates as catalysts for bleaching agents is well known in the art. For example, U.S. Pat. No. 4,119,557, issued to Postlethwaite, discloses the use of iron-polycarboxyamine complexes with hydrogen peroxide releasing substances to clean fabrics. Similarly, U.S. Pat. No. 5,244,594 (Favre et al.), U.S. Pat. No. 5,246,621 (Favre et al.), U.S. Pat. No. 5,194,416 (Jureller et al.), and U.S. Pat. No. 5,314,635 (Hage et al.) describe the use of manganese complexes of nitrogen- (or other heteroatom-) coordinated macrocycles as catalysts for peroxy compounds.

The utility of compounds of this type has motivated researchers to develop new ligands that both stabilize the catalyst complex and that are able to withstand an oxidative environment. Promising ligands in this respect are the tetraamido macrocycles represented by structure 10 shown in FIG. 1 which, when complexed with a transition metal such as iron, afford particularly good dye transfer inhibition capabilities.

An azide-based synthesis of the macrocycle is described by Collins et al. in *J. Am. Chem. Soc.*, vol. 113, No. 22, page 8419 (1991). A problem with this synthesis is that it produces the tetraamido macrocycle in yields of only about 12% (starting from 1,2-phenylenediamine, as shown in the scheme at page 8422 of the article) and employs isolation techniques which cannot be adapted to large scale production. (Note: The identical synthesis is described by Erich S. Uffelman in his Ph.D. dissertation at California Institute of Technology (1992) and is the work upon which the synthesis of the journal article is based.)

Another synthetic route to the macrocycle is described in U.S. Pat. No. 5,853,428, issued also to the same Collins, and employs a ring forming strategy that is the reverse of the earlier published synthesis. In this synthesis, α-aminoisobutyric acid is used as a starting material to form the intermediate diacid 18 shown in FIG. 1, which is then coupled with an aryl diamine to yield the macrocycle (as shown in the scheme at col. 15 of the patent). This later synthesis, described by Collins as now being his preferred synthesis, provides the macrocycle structure in two steps and in an improved overall yield of about 18% (starting from diethyl malonyl dichloride). (Note: The identical synthesis is described by Scott W. Gordon-Wylie in his Ph.D. dissertation at Carnegie Mellon University (1995) and is the work upon which the synthesis of the patent is based.)

However, a number of problems exist with the Collins patent synthesis. For one, α-aminoisobutyric acid is a relatively expensive starting material. Further, the yield of the diacid is only about 50–60% from that starting material and usually requires further purification. Additionally, the first step, a double coupling, is said to require 72–144 hours for completion, while the second step, a ring closure, requires 48–110 hours. Still further, the use of large amounts of anhydrous pyridine as solvent are apparently required in both steps, which is commercially prohibitive. For commercial purposes, a more efficient and less expensive synthesis of the tetraamido macrocycle is required than is provided by either of the two prior art syntheses just described.

SUMMARY OF THE INVENTION

Briefly, the present invention comprises an improved synthesis of tetraamido-macrocyclic ligands as exemplified by 5,6-benzo-3,8,11,13-tetraoxo-2,2,9,9-tetramethyl-12,12-diethyl-1,4,7,10-tetraazacyclotridecane, $H_4$. In the improved synthesis, a previously unreported diamidodiol is formed in high yield from diethylmalonyl dichloride and the relatively inexpensive starting material 2-amino-2-methyl-1-propanol. The novel diamidodiol is then oxidized to the diacid used in the synthesis of the Collins patent described above. Coupling of the diacid with an aryl diamine then yields the macrocycle according to the procedure found in the same patent. However, in the improved synthesis of the present invention, not only is a less expensive starting material used but the yield of the diacid is increased from the 50–60 % obtained in the prior art to approximately 74%. Additionally, the improved synthesis avoids the use of anhydrous pyridine solvent, which is also expensive. Further, the present invention produces an easily isolable product (i.e., the diacid) in excellent purity, whereas in the Collins patent the synthesis involves a tedious work-up procedure and produces a product that typically requires recrystallization. The present invention requires that the intermediate diacid be made in two steps, but these steps are considerably more viable from a commercial standpoint than the Collins synthesis, both in terms of simplicity of performance and cost.

DETAILED DESCRIPTION OF THE INVENTION

Figure 1:
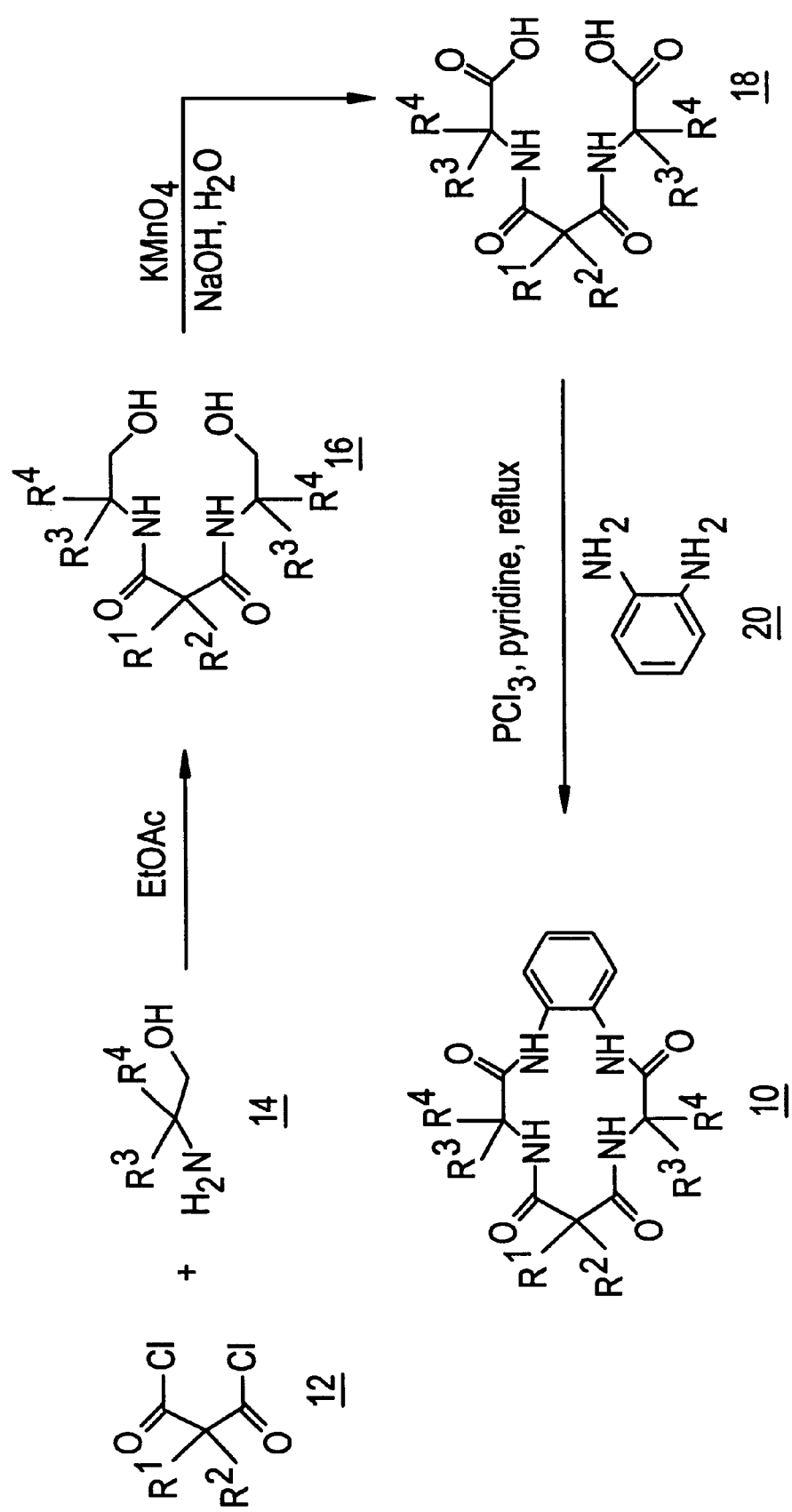
FIG. 1 is a flowchart illustrating the improved synthesis of the tetraamido macrocycle using the novel diamidodiol precursor according to the present invention.

FIG. 1 illustrates a reaction sequence for preparing the tetraamido macrocycle 10 in a simpler and more commercially viable manner than has previously been reported. In the preferred reaction sequence, one mole of diethylmalonyl dichloride (dichloride 12) ($R^1=R^2=$ethyl) is allowed to react with two to four moles of 2-amino-2-methyl-1-propanol (aminoalcohol 14) ($R^3=R^4=$methyl) in an appropriate solvent. Ethyl acetate is the preferred solvent, however, other solvents such as tetrahydrofura (THF), diethyl ether, acetonitrile or even water can also be used. 2-Amino-2-methyl-1-propanol is commercially available in large quantities, for example from Angus Chemical Company, and costs approximately $1.65/pound. The relative inexpensiveness of the aminoalcohol 14 makes it an attractive starting material for preparing the macrocycle 10 in commercially viable quantities.

Ideally, four molar equivalents of the aminoalcohol 14 are employed in the reaction such that two moles are made to react with the dichloride 12 while the remaining two moles act as a base to scavenge the hydrogen chloride (HCl) that is generated during the reaction. A tertiary base such as triethylamine may also be used as an HCl scavenger, in which case only two molar equivalents of the aminoalcohol 14 are required. When ethyl acetate is used as the solvent, the desired product (diamidodiol 16), together with the ammonium salt produced by reaction of HCl with the aminoalcohol 14, precipitate from the reaction mixture. Thus, in what affords a highly desirable workup for commercial purposes, the solid products are simply collected by filtration and washed with water to remove the ammonium salt. After the washing, the remaining solid is the diamidodiol 16 in high purity and yield.

With continued reference to FIG. 1, the diamidodiol 16 prepared in the previous step is suspended in an alkaline aqueous solution and is oxidized with potassium permanganate ($KMnO_4$) under controlled reaction temperature conditions to yield a mixture of the diacid 18 and manganese dioxide solids. Preferably the temperature of the reaction mixture is not allowed to exceed about 70 degrees C. during the addition of the $KMnO_4$. It will be appreciated that other oxidants known in the art can be used in place of $KMnO_4$. After quenching the mixture with ethanol to destroy any excess $KMnO_4$, the reaction mixture is filtered to remove the manganese dioxide solids. The filtrate is then strongly acidified, which causes precipitation of the diacid 18. The diacid 18 is collected by filtration and air-dried and is sufficiently pure to be used without further purification (the product is pure by $^{13}$C-NMR). Thus, this second step again allows for a simple workup procedure and one that is industrially (and environmentally) very favorable. Actual examples of the procedures used for preparing compounds 16 and 18 are given later below.

The diamidodiol 16 is a previously unreported compound. The ability to prepare the diamidodiol 16 in high yield and purity allows the diacid 18 to also be prepared in higher yield while using a starting material and solvents that are less expensive (and environmentally friendly), and with workup methods that are more amenable to commercial scale production than is possible with the prior art synthesis found in the Collins patent. This makes preparation of the macrocycle 10 in commercially reasonable amounts significantly more feasible.

As indicated in FIG. 1, the tetraamido macrocycle 10 itself is prepared by reaction of the diacid 18 with 1,2-phenylenediamine(phenylenediamine 20) using the phosphorous trichloride ($PCl_3$) coupling method previously described in the Collins patent. Specifically,the diacid 18, phenylenediamine 20 and pyridine are combined and heated to 50–60 degrees C. $PCl_3$ is then added and the mixture refluxed for forty-eight hours. The contents are acidified with HCl and extracted with methylene chloride. The combined organic layers are washed with dilute aqueous HCl followed by water. Rotary evaporation of the organic extracts yields the crude tetraamido macrocycle 10.

It will be apparent to those with ordinary skill in the art that the synthesis which has been described can easily be adapted for the preparation of tetraamido macrocyclic ligands having substituents other than that of the exemplified macrocycle 10. For example, in the first acylation step, a malonyl dihalide having $R^1$ and/or $R^2$ other than diethyl can be reacted with an aminoalcohol having $R^3$ and/or $R^4$ other than dimethyl to yield a variety of diamidodiols. (The synthesis of a number of variously disubstituted malonyl dichlorides is described later below.) Similarly, in the last coupling/cyclization step, a 1,2-phenylenediamine having substituents at any or all of the 3-, 4-, 5- and 6-positions of the phenyl ring can be employed to yield any number of what can generically be referred to as 1,2-bis(2-aminoalkanamido)benzenes. Thus, and referring to FIG. 1 one last time, $R^1$, $R^2$, $R^3$ and $R^4$ may be any of a wide variety of different substituents such as hydrogen, alkyl (including short and long chains), alkenyl, aryl (including benzyl), etc., and the phenyl ring can be substituted with any of a number of substituents such as nitro, methoxy, halo, etc., as are all well known in the art, in order to make any number of differently substituted macrocycles 10.

The following two examples illustrate the preferred methods for preparing compounds 16 and 18 according to the present invention:

EXAMPLE 1
Preparation of Diamidodiol (16)

2-Methyl-2-amino-1-propanol (42.9 grams, 0.482 moles) was dissolved in ethyl acetate (700 mL) in a 2 L round-bottom flask fitted with a mechanical stirrer. Diethylmalonyl dichloride (22.9 grams, 0.116 moles) was dissolved in ethyl acetate (30 mL) and added dropwise to the stirring solution of the aminoalcohol. A white precipitate begins to form immediately. After addition was complete, the reaction mixture was stirred for two hours at room temperature. Rotary evaporation of the solvent affords a white solid, which is shaken with water and filtered. The wet filter cake consisting of the crude product is used as-is in the next step.

EXAMPLE 2
Preparation of Diacid 18

The crude diamidodiol from Example 1 is slurried in water (300 mL). Sodium hydroxide (9.3 grams), predissolved in a small amount of water, is added to the slurry. The aqueous slurry is heated to about 50 degrees C. and stirred vigorously. Powdered potassium permanganate (46 grams) is added in small portions at such a rate that the temperature of the reaction mixture does not exceed 70 degrees C. After the addition of the permanganate is complete, the mixture is heated for an additional hour at 60 degrees C. A small amount of ethanol is added to destroy any remaining permanganate and the reaction mixture is filtered through a plug of Celite. The clear filtrate is collected, cooled in an ice-bath, and acidified with concentrated HCl until the pH is less than 2. The white solid that precipitates is collected by filtration, washed well with water, and dried in a vacuum oven overnight. The final weight of the product is 28.4 grams (74% yield based upon starting malonyl dichloride). The product is pure by $^{13}$C-NMR and is identical to an authentic sample prepared by other means as indicated by NMR, IR, and melting point analyses.

Figure 2:
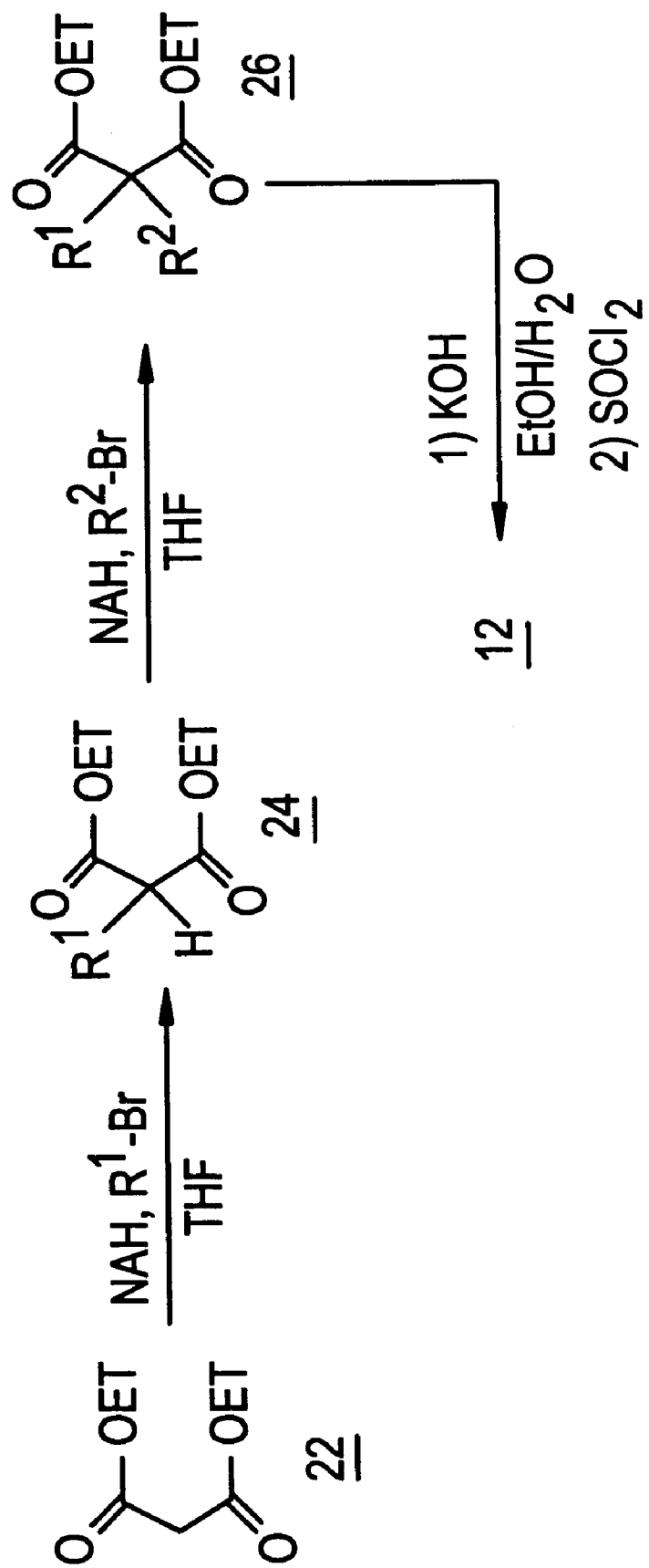
FIG. 2 is a reaction sequence illustrating how variously substituted malonyl dichloride starting materials may be prepared.

FIG. 2 illustrates a synthetic route for the preparation of variously substituted malonyl dichlorides. The general synthetic procedure involves the stepwise alkylation of diethylmalonate(22). Diethylmalonate 22 is reacted in tetrahydrofuran(THF) with one equivalent of sodium hydride (NaH) and one equivalent of an alkylating agent such as an alkyl halide (e.g., $R^1$—Br). The resulting monosubstituted diethylmalonate 24 is then reacted with a second equivalent of NaH and one equivalent of a second alkylating agent (e.g., $R^2$—Br). (Note: Even when $R^1=R^2$, it is preferable that the first equivalent of NaH and the first equivalent of alkylating agent be allowed to react to completion before the second equivalent of NaH and the second equivalent of the same alkylating agent are added to the reaction mixture.) If the reaction is stopped before the second equivalents of reagents are added, then a monosubstituted malonate is obtained. The alkylation can be accomplished using other bases and solvents as are well-known in the art.

The disubstituted diethylmalonate (26) obtained from the stepwise alkylation is saponified using potassium hydroxide and ethanol and then chlorinated using thionyl chloride. The saponification can be accomplished using many other reagents, as are well-known in the art, and the chlorination can be accomplished with many other chlorinating agents, such as oxalyl chloride, $PCl_3$, $PCl_5$, etc.

The procedure outlined provides a general method for preparing substituted malonyl dichlorides 12 where $R^1$ and $R^2$ are the same or different. Examples 3, 4 and 5 below illustrate specific syntheses that utilize the reaction sequences illustrated in FIG. 2.

EXAMPLE 3

Alkylations

Dipentyl Diethylmalonate (26, $R^1=R^2$=pentyl)

To a stirring solution of diethylmalonate (8.0 g, 50 mmol) in THF (100 mL, 0.5 M) was added sodium hydride (1.2 g, 50 mmol). The solution began bubbling and an exothermic reaction occurred. The reaction eventually turned clear and then pentyl bromide (6.2 mL, 50 mmol) was added. The reaction was refluxed for 20 hours and then cooled to room temperature. Another equivalent of NaH (1.2 g, 50 mmol) was added to the cloudy white mixture which was then stirred for 4 hours at room temperature. Another equivalent of pentyl bromide (6.2 mL, 50 mmol) was added and the reaction was refluxed for 20 hours. The reaction was cooled to room temperature and filtered to remove the precipitated sodium bromide. The mother liquor was collected and concentrated in vacuo to a yellow oil. The crude product was then distilled under vacuum (140° C.) to afford 9.34 g (62%) of pure product.

Dioctyl Diethylmalonate (26, $R^1=R^2$=octyl)

To a stirring solution of diethylmalonate (16.0 g, 100 mmol) in THF (200 mL, 0.5 M) was added sodium hydride (2.4 g, 100 mmol). The solution began bubbling and an exothermic reaction occurred. The reaction eventually turned clear and then octyl bromide (17.3 mL, 100 mmol) was added. The reaction was refluxed for 20 hours and then cooled to room temperature. Another equivalent of NaH (2.4 g, 100 mmol) was added to the cloudy white mixture which was then stirred for 4 hours at room temperature. Another equivalent of octyl bromide (17.3 mL, 100 mmol) was added and the reaction was refluxed for 20 hours. The reaction was cooled to room temperature and filtered (NaBr). The mother liquor was collected and concentrated in vacuo to a yellow oil. The crude product was then distilled under vacuum (250° C.) to afford 23.4 g (64%) of pure product.

Dodecylmethyl Diethylmalonate (26, $R^1$=methyl, $R^2$=dodecyl)

To a stirring solution of commercially available methyl diethylmalonate (17.4 g, 100 mmol) in THF (200 mL, 0.5 M) was added sodium hydride (2.4 g, 100 mmol). The solution began bubbling and an exothermic reaction occurred. The reaction eventually turned clear and then dodecyl bromide (24.0 mL, 100 mmol) was added. The reaction was refluxed for 20 hours and then cooled to room temperature and filtered (NaBr). The mother liquor was collected and concentrated in vacuo to a yellow oil. The crude product was then distilled under vacuum (239° C.) to afford 17.7 g (52%) of pure product.

Hexadecylmethyl Diethylmalonate (26, $R^1$=methyl, $R^2$=hexadecyl)

To a stirring solution of methyl diethylmalonate (17.4 g, 100 mmol) in THF (200 mL, 0.5 M) was added sodium hydride (2.4 g, 100 mmol). The solution began bubbling and an exothermic reaction occurred. The reaction eventually turned clear and then hexadecyl bromide (30.5 mL, 100 mmol) was added. The reaction was refluxed for 20 hours and then cooled to room temperature and filtered (NaBr). The mother liquor was collected and concentrated in vacuo to a yellow oil. The crude product was then distilled under vacuum (275° C.) to afford 13.8 g (35%) of pure product.

Methyloctyl Diethylmalonate (26, $R^1$=methyl $R^2$=octyl)

To a stirring solution of methyl diethylmalonate (17.4 g, 100 mmol) in THF (200 mL, 0.5 M) was added sodium hydride (2.4 g, 100 mmol). The solution began bubbling and an exothermic reaction occurred. The reaction eventually turned clear and then octyl bromide (17.3 mL, 100 mmol) was added. The reaction was refluxed for 20 hours and then cooled to room temperature and filtered (NaBr). The mother liquor was collected and concentrated in vacuo to a yellow oil. The crude product was then distilled under vacuum (197° C.) to afford 15.2 g (53%) of pure product.

Methylpentyl Diethylmalonate (26, $R^1$=methyl, $R^2$=pentyl)

To a stirring solution of methyl diethylmalonate, (17.4 g, 100 mmol) in TBF (200 mL, 0.5 M) was added sodium hydride (2.4 g, 100 mmol). The solution began bubbling and an exothermic reaction occurred. The reaction eventually turned clear and then pentyl bromide (12.4 mL, 100 mmol) was added. The reaction was refluxed for 20 hours and then cooled to room temperature and filtered (NaBr). The mother liquor was collected and concentrated in vacuo to a yellow oil. The crude product was then distilled under vacuum (160° C.) to afford 12.1 g (50%) of pure product.

EXAMPLE 4

Saponifications

Dipentylmalonic Acid

To a stirring mixture of dipentyl diethylmalonate (9.0 g, 30 mmol) in water (60 mL) and ethanol (60 mL) was added KOH pellets (16.8 g, 300 mmol). The cloudy mixture was then refluxed overnight where it became clear. The solvent was concentrated in vacuo to a white solid. The solid was dissolved in water and extracted with ether (2x). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 5.6 g of pure product (76%).

Dioctylmalonic Acid

To a stirring mixture of dioctyl diethylmalonate (15.0 g, 39 mmol) in water (78 mL) and ethanol (78 mL) was added KOH pellets (21.8 g, 390 mmol). The cloudy mixture was then refluxed overnight where it became clear. The solvent was concentrated in vacuo to a white solid. The solid was dissolved in water and extracted with ether (2x). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 8.4 g of pure product (67%).

Dibenzylmalonic Acid

To a stirring mixture of commercially available dibenzyl diethylmalonate (20.0 g, 64 mmol) in water (128 mL) and ethanol (128 mL) was added KOH pellets (35.9 g, 640 mmol). The cloudy mixture was then refluxed overnight where it became clear. The solvent was concentrated in vacuo to a white solid. The solid was dissolved in water and extracted with ether (2x). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 13.8 g of pure product (84%).

Dodecylmethylmalonic Acid

To a stirring mixture of dodecylmethyl diethylmalonate (17.7 g, 52 mmol) in water (100 mL) and ethanol (100 mL) was added KOH pellets (29.0 g, 520 mmol). The cloudy mixture was then refluxed overnight where it became clear. The solvent was concentrated in vacuo to a white solid. The solid was dissolved in water and extracted with ether (2×). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 13.0 g of pure product (84%).

Hexadecylmethylmalonic Acid

To a stirring mixture of hexadecylmethyl diethylmalonate (13.8 g, 35 mmol) in water (78 mL) and ethanol (78 mL) was added KOH pellets (21.8 g, 390 mmol). The cloudy mixture was then refluxed overnight where it became clear. The solvent was concentrated in vacuo to a white solid. The solid was dissolved in water and extracted with ether (2×). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 10.3 g of pure product (84%).

Methyloctylmalonic Acid

To a stirring mixture of methyloctyl diethylmalonate (6.8 g, 25 mmol) in water (50 mL) and ethanol (50 mL) was added KOH pellets (15.0 g, 250 mmol). The cloudy mixture was then refluxed overnight where it became clear. The solvent was concentrated in vacuo to a white solid. The solid was dissolved in water and extracted with ether (2×). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 4.3 g of pure product (75%).

Methylpentylmalonic Acid

To a stirring mixture of methylpentyl diethylmalonate (12.1 g, 50 mmol) in water (100 mL) and ethanol (100 mL) was added KOH pellets (29 g, 500 mmol). The cloudy mixture was then refluxed overnight where it became clear. The solvent was concentrated in vacuo to a white solid. The solid was dissolved in water and extracted with ether (2×). The water layer was then acidified with concentrated HCl and a solid precipitated out of solution. The white solid was filtered and the resulting mother liquor was extracted with ether in order to isolate any additional product. The combined organic layers were concentrated in vacuo and the resulting white solid was added to the filtered solid and dried in a vacuum oven. This afforded 7.2 g of pure product (77%)

EXAMPLE 5

Chlorinations

Dipentylmalonyl Dichloride (12, $R^1=R^2$=pentyl)

A solution of dipentylmalonic acid (2.5 g, 10.2 mmol) in thionyl chloride (5.25 mL, 72 mmol) was heated to 60° C. and stirred for 16 hours. The reaction was then cooled to room temperature and the excess thionyl chloride was removed in vacuo. The resulting crude diacyl chloride (2.8 g, 100%) was pure by NMR analysis and was taken directly on to the next reaction (no purification needed).

Dioctylmalonyl Dichloride (12, $R^1=R^2$=octyl)

A solution of dioctylmalonic acid (8.0 g, 24.4 mmol) in thionyl chloride (12.5 mL, 170.8 mmol) was heated to 60° C. and stirred for 16 hours. The reaction was then cooled to room temperature and the excess thionyl chloride was removed in vacuo. The resulting crude diacyl chloride (8.9 g, 100%) was pure by NMR analysis and was taken directly on to the next reaction (no purification needed).

Dibenzylmalonyl dichloride (12, $R^1=R^2$=benzyl)

A solution of dibenzylmalonic acid (8.0 g, 31.3 mmol) in thionyl chloride (16 mL, 218.8 mmol) was heated to 60° C. and stirred for 16 hours. The reaction was then cooled to room temperature and the excess thionyl chloride was removed in vacuo. The resulting crude diacyl chloride (9.1 g, 100%) was pure by NMR analysis and was taken directly on to the next reaction (no purification needed).

Dodecylmethylmalonyl Dichloride (12, $R^1$=methyl, $R^2$=dodecyl)

A solution of dodecylmethylmalonic acid (7.18 g, 24.4 mmol) in thionyl chloride (12.5 mL, 170.8 mmol) was heated to 60° C. and stirred for 16 hours. The reaction was then cooled to room temperature and the excess thionyl chloride was removed in vacuo. The resulting crude diacyl chloride (8.1 g, 100%) was pure by NMR analysis and was taken directly on to the next reaction (no purification needed).

Hexadecylmethylmalonyl Dichloride (12, $R^1$=methyl, $R^2$=hexadecyl)

A solution of hexadecylmethylmalonic acid (8.54 g, 24.4 mmol) in thionyl chloride (12.5 mL, 170.8 mmol) was heated to 60° C and stirred for 16 hours. The reaction was then cooled to room temperature and the excess thionyl chloride was removed in vacuo. The resulting crude diacyl chloride (9.4 g, 100%) was pure by NMR analysis and was taken directly on to the next reaction (no purification needed).

Methyloctylmalonyl Dichloride (12, $R^1$=methyl, $R^2$=octyl)

A solution of methyloctylmalonic acid (4.3 g, 18.7 mmol) in thionyl chloride (9.5 mL, 130 mmol) was heated to 60° C. and stirred for 16 hours. The reaction was then cooled to room temperature and the excess thionyl chloride was removed in vacuo. The resulting crude diacyl chloride (5.0 g, 100%) was pure by NMR analysis and was taken directly on to the next reaction (no purification needed).

Methylpentylmalonyl dichloride (12, $R^1$=methyl, $R^2$=pentyl)

A solution of Methylpentylmalonic acid (3.5 g, 18.7 mmol) in thionyl chloride (9.5 mL, 130 mmol) was heated to 60° C and stirred for 16 hours. The reaction was then cooled to room temperature and the excess thionyl chloride was removed in vacuo. The resulting crude diacyl chloride (4.2 g, 100%) was pure by NMR analysis and was taken directly on to the next reaction (no purification needed).

Although the present invention has been described in terms of a presently preferred embodiment, it is to be understood that such disclosure is not to be interpreted as limiting. Various alterations and modifications in addition to those just described will no doubt become apparent to those skilled in the art after having read the above disclosure. Accordingly, it is intended that the appended claims be interpreted as covering all alterations and modifications as fall within the true spirit and scope of the invention.

What is claimed is:

1. A method for synthesizing a diamidodiol having the structural formula:

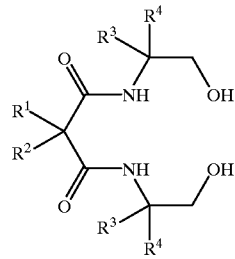

wherein $R^1$, $R^2$ are different, but $R^3$ and $R^4$ are the same or different and are selected from the group consisting of hydrogen, alkyl (including short and long chain), alkenyl, and aryl (including benzyl), comprising:
    forming a reaction solution comprised of a solvent, a first quantity of an aminoalcohol and a second quantity of a malonyl dichloride;
    separating a product mixture from the reaction solution, the product mixture containing the diamidodiol; and
    isolating the product diamidodiol from the product mixture.

2. The method of claim 1 wherein the reaction solution is formed by dissolving the first quantity of aminoalcohol in a first volume of the solvent to form a first solution;
    dissolving the second quantity of the malonyl dichloride in a second volume of the solvent to form a second solution; and
    combining the first and second solutions to form the reaction solution.

3. The method of claim 2 where in the second solution is added dropwise to the first solution.

4. The method of claim 1 wherein the first quantity and the second quantity provide a molar ratio of amino alcohol to malonyl dichloride in the range of approximately 2:1 to 4:1.

5. The method of claim 1 wherein the solvent is selected from the group consisting of ethyl acetate, tetrahydrofuran, diethyl ether, acetonitrile and water.

6. The method of claim 1 wherein the step of separating the product mixture from the reaction solution comprises evaporating the solvent.

7. The method of claim 1 wherein the step of separating the product mixture comprises filtration.

8. The method of claim 1 wherein the step of isolating the diamidodiol comprises washing the product mixture with water after the product mixture is separated from the reaction solution.

9. A method for preparing a diacid having the structural formula:

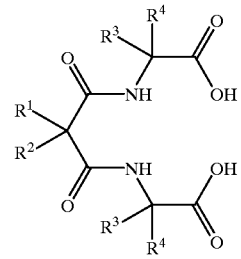

comprising the step of:
    oxidizing a diamidodiol having the structural formula

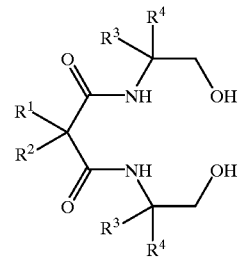

wherein $R^1$, $R^2$ are different, but $R^3$ and $R^4$ are the same or different and are selected from the group consisting of hydrogen, alkyl (including short and long chain), alkenyl, and aryl (including benzyl).

10. The method of claim 9 wherein the step of oxidizing the diamidodiol comprises adding $KMnO_4$ to an alkaline suspension comprised of the diamidodiol and water.

11. The method of claim 9 wherein the diamidodiol is prepared in prior steps comprising:
    forming a reaction solution comprised of a solvent, a first quantity of an aminoalcohol and a second quantity of a malonyl dichloride;
    separating a product mixture from the reaction solution; and
    isolating the product diamidodiol from the product mixture.

* * * * *